US006831747B2

(12) United States Patent
Ferrell et al.

(10) Patent No.: US 6,831,747 B2
(45) Date of Patent: Dec. 14, 2004

(54) SPECTROMETRY AND FILTERING WITH HIGH REJECTION OF STRAY LIGHT

(75) Inventors: Thomas L. Ferrell, Knoxville, TN (US); Thomas G. Thundat, Knoxville, TN (US)

(73) Assignee: UT-Battelle, LLC, Oak Ridge, TN (US)

(*) Notice: Subject to any disclaimer, the term of this patent is extended or adjusted under 35 U.S.C. 154(b) by 114 days.

(21) Appl. No.: 10/338,614

(22) Filed: Jan. 8, 2003

(65) Prior Publication Data

US 2004/0130722 A1 Jul. 8, 2004

(51) Int. Cl.[7] .................... G01N 21/55; G01N 21/00
(52) U.S. Cl. .................... 356/445; 356/72; 356/73
(58) Field of Search ............... 356/445, 72–73

(56) References Cited

U.S. PATENT DOCUMENTS

| 5,018,865 | A | 5/1991 | Ferrell |
| 5,785,898 | A | 7/1998 | Hofmeister |
| 5,986,808 | A | 11/1999 | Wang |
| 6,034,809 | A | 3/2000 | Anemogiannis |
| 6,122,091 | A | 9/2000 | Russell |

OTHER PUBLICATIONS

C. Jung, et al., "Integrated Optics Waveguide Modulator Based on Surface Plasmon Resonance", Journal of Lightwave Technology, Oct. 1994, pp. 1802–1806, vol. 12, No. 10.

Yu E. Lozovik, et al., From Two–Beam Surface Plasmon Interaction to Femtosecond Surface Optics and Spectroscopy, Physics Letters A, Oct. 30, 2000, pp. 127–132.

W.A. Challener, et al., "A Multilayer Grating–Based Evanescent Wave Sensing Technique", Sensors and Actuators B, Jun. 22, 2000, pp. 42–46.

Gilles Tessier, "Non Linear Optics and Magneto–Optics in Ultrathin Metallic Films", Applied Surface Science, 2000, pp. 175–185.

J. Tominaga, "Local Plasmon Photonic Transistor" Applied Physics Letters, Apr. 23, 2001, pp. 2417–2419, vol. 78, No. 17.

Primary Examiner—Gregory J. Toatley, Jr.
Assistant Examiner—Amanda Merlino
(74) Attorney, Agent, or Firm—Kirk A. Wilson

(57) ABSTRACT

A microoptoelectromechanical integrated spectrometer with a photonic element assembly having metal foil removably disposed on a first transparent substrate surface, the substrate having no foil on any other surface. A means is provided for directing source photons that are reflected from or transmitted through a sample, over a range of angles of incidence, into the transparent substrate and onto the metal foil such that source photons are incident at the Brewsters angle. A means is also provided for detecting an induced exponential field in the metal foil. A means is also provided for relating the induced exponential field to a known exponential field for the sample and determining the identity of the sample. The spectrometer performs ultraviolet-to-visible-to-infrared spectroscopy using photon tunneling and surface plasmon excitation.

20 Claims, 4 Drawing Sheets

SPECTROMETRY AND FILTERING WITH HIGH REJECTION OF STRAY LIGHT

The United States Government has rights in this invention pursuant to contract no. DE-AC05-000R22725 between the United States Department of Energy and UT-Battelle, LLC.

FIELD OF THE INVENTION

The present invention relates to a spectrometer or filter device. In particular, the present invention relates to a spectrometer device in which the wavelengths of a beam of photons are controllably detected and measured in relative intensity after being distributed to a set of photon receptor elements via a thin metal foil. Further, the present invention relates to spectral information in the source beam of photons that is subject to differentiation by wavelength and distance within the exponential field within one wavelength of the foil. The separation of wavelengths into multiple parts occurs by the stimulation of surface plasmons in the metal foil at the Brewster angle for each incident wavelength or by detection of the decay length of an evanescent field. An embodiment of the invention employs surface plasmons and provides filtering of all wavelengths not incident at the Brewster angle due to the high reflectivity of the metal foil at angles other than Brewster's angle.

BACKGROUND OF THE INVENTION

The use of surface plasmons to filter and hence to separate wavelengths of photons by using a supplementary dielectric second layer has been described in U.S. Pat. No. 5,986,808 by Wang and in U.S. Pat. No. 6,122,091 by Russell, both herein incorporated by reference. Each of these requires a second layer of dielectric beyond a metal foil that is essential to the phenomena considered and the filtering is not therefore solely dependent upon the surface plasmons. Nor is the case considered in these references one in which the surface plasmons are detected within one wavelength of the metal foil.

Similarly the use of surface plasmons in controlling photons by using a second dielectric layer has been described in U.S. Pat. No. 6,034,809 by Anemogiannis and is herein incorporated by reference. Anemogiannis teaches optical plasmon-wave attenuation and modulation structures for controlling the amount of coupling between a guided optical signal and a surface plasmon wave, but the second-layer required must be controlled by another device so as to cause a change in optical index of the second layer. Anemogiannis employs no condition in which the surface plasmons are associated with spectrometry or filtering without the presence of the controlling dielectric layer.

In summary, prior art has the necessity of a special second layer and the lack of use of surface plasmons in the exponentially decaying electric field provided by the surface plasmons within one wavelength of the surface. Therefore, these comprise prior art utilizing different physical phenomena to actually act upon the photons than is described in the present invention. Further they do not provide a means of differentiating the signal so as to determine distance to the surface.

The following background publications are herein incorporated by reference:
1. E. Kretschmann, E., Rather, H., Z. *Naturforsch*, 216, 398–410, (1968).
2. Otto, A., Z. *Physik*, 216, 398–410, (1968).
3. Welford, K. R., et al., "Coupled Surface plasmons in a Symmetric System," *Journal of Modern Optics*, Vol. 35, No. 9, Pp.1467–1483, 1988.
4. Hoyt, Clifford C., "Towards Higher Res, Lower Cost Quality Color and Multispectral Imaging," Advanced Imaging, pp. 53–55, April 1995.
5. Kajenski; "Tunable Optical Fiber Using Long-Range Surface Plasmons"; *Society of Photo-Optical Instrumentation Engineers*; Vol. 36, No. 19 Pp. 1537–1541, May 1997.
6. Wang, Yu, "Voltage-induced Color Selective Absorption with Surface Plasmons," *Appl. Phys. Lett.*, Vol. 67, No. 19, Pp. 2759–2761, Nov. 6, 1995.
7. Caldwell et al.; "Surface-Plasmon Spatial Light Modulators Based on Liquid Crystal"; *Applied Optics*; Vol. 31, No. 20; Pp. 3880–3891, Jul. 10, 1992;
8. Jung et al.; "Integrated Optics Waveguide Modulator Based on Surface Plasmon Resonance"; *Journal of Lightwave Technology*; Vol. 12, No. 10, October 1994; Pp. 1802–1806.
9. Lozovik Y E; Merkulova S P; Nazarov M M; Shkurinov A P., "From two-beam surface plasmon interaction to femtosecond surface optics and spectroscopy" *Physics Letters A*, Vol 276, Iss 1–4, Pp. 127–132, Oct. 30, 2000.
10. Challener W. A.; Edwards J. D., McGowan R. W., Skorjanec J., Yang Z., "A multilayer grating-based evanescent wave sensing technique", *Sensors* and *Actuators B-Chemica*, Vol 71, Iss1-2, Pp. 42–46, Nov. 15, 2000.
11. Tessier G; Beauvillain P., "Non linear optics and magneto-optics in ultrathin metallic films", *Applied Surface Science*, Vol 164, Pp 175–185 Sep. 1, 2000.
12. Tominaga et al, *Appl. Phys. Let*, Vol. 78, No. 17, Pp. 2417–2419 Apr. 23, 2001.
13. Ferrell et al., U.S. Pat. No. 5,018,865; issued May 28, 1991.

BRIEF SUMMARY OF THE INVENTION

The tunneling of photons from a region of total-internal reflection is engendered by a probe or detector situated within one photon wavelength of the reflecting surface. The tunneling signal received is converted immediately thereafter to an electronic signal after being transmitted by an optical fiber or waveguide to a detector. This principle has long been used in phenomena of frustrated total internal reflection in the optical region of the spectrum in the case without a metal foil. The probe or detector is positioned with modern piezoelectric crystals to an accuracy of 0.0005 nm by using data on the ratio of the derivative of the signal with respect to wavelength to the derivative with respect to distance. If an unknown wavelength is introduced to the system, the ratio of the aforementioned derivatives can be thence remeasured to produce the value of the wavelength. If multiple wavelengths are introduced in combination, then a second photonic element is required in order to delineate the wavelengths and permit the above-mentioned measurements to obtain the intensity of each wavelength relative to the calibration wavelength. This additional element is a thin metal foil (typically 10–100 nm thick) placed on the reflecting surface. Each wavelength will induce surface plasmon quanta in the foil at an angle unique to that wavelength (Brewster's angle) with a tolerance of milliradians. The surface plasmon field is of the same functionality (exponential in the tunneling gap) as the evanescent field in the original case, but tunneling now occurs only for a single wavelength with a degree of broadening due to damping of surface plasmons of the combined waves. The angle of incidence is thereafter successively changed by minute amounts in order to permit successive wavelengths and provide a tunneling signal. In this way a complete spectrum of the incident photons is obtained by repeated measurement of the derivative ratio or by simultaneously doing so with multiple probes or an array of detectors. A probe is produced by etching silicon dioxide on a silicon wafer or in the core of an optical fiber. Simultaneous measurement at many wavelengths can alternatively be used if the incident photons are dispersed in wavelength to any given degree if an array of charged-coupled devices or other solid-state devices are formed into a compact two-dimensional array and placed in the near zone of the foil. The resulting probe or detector is driven to resonance using similar electronics to that used for other micromechanical systems (e.g., micro-cantilevers, membranes, etc.). By tracking the bending and resonance behavior of the probe using the tunneling signal, the probe simultaneously functions as a sensor in a large variety of sensing applications. Therefore, the spectrum of a targeted sample is simultaneously obtained while sensing other properties of the sample. The sample may be an element or compound in fluid form, a biological material, or it may simply be desired to measure a physical property of the environment during the process of acquisition of a spectrum. Spectroscopies enabled on silicon by this device include all of the ultraviolet, visible, and infrared spectroscopies, Raman spectroscopy, and photometry. A special advantage is the high stray-light rejection factor provided by the metal foil for wavelengths not incident at the Brewster angle.

One embodiment of the invention is a microoptoelectromechanical integrated spectrometer with a photonic element assembly having metal foil removably disposed on a first transparent substrate surface, the substrate having no foil on any other surface. A means is provided for directing source photons that are reflected from or transmitted through a sample, over a range of angles of incidence, into the transparent substrate and onto the metal foil such that source photons are incident at the Brewsters angle. A means is also provided for detecting an induced exponential field in the metal foil. A means is also provided for relating the induced exponential field to a known exponential field for the sample and determining the identity of the sample. The spectrometer performs ultraviolet-to-visible-to-infrared spectroscopy using photon tunneling and surface plasmon excitation.

DETAILED DESCRIPTION OF THE INVENTION

Figure 1:
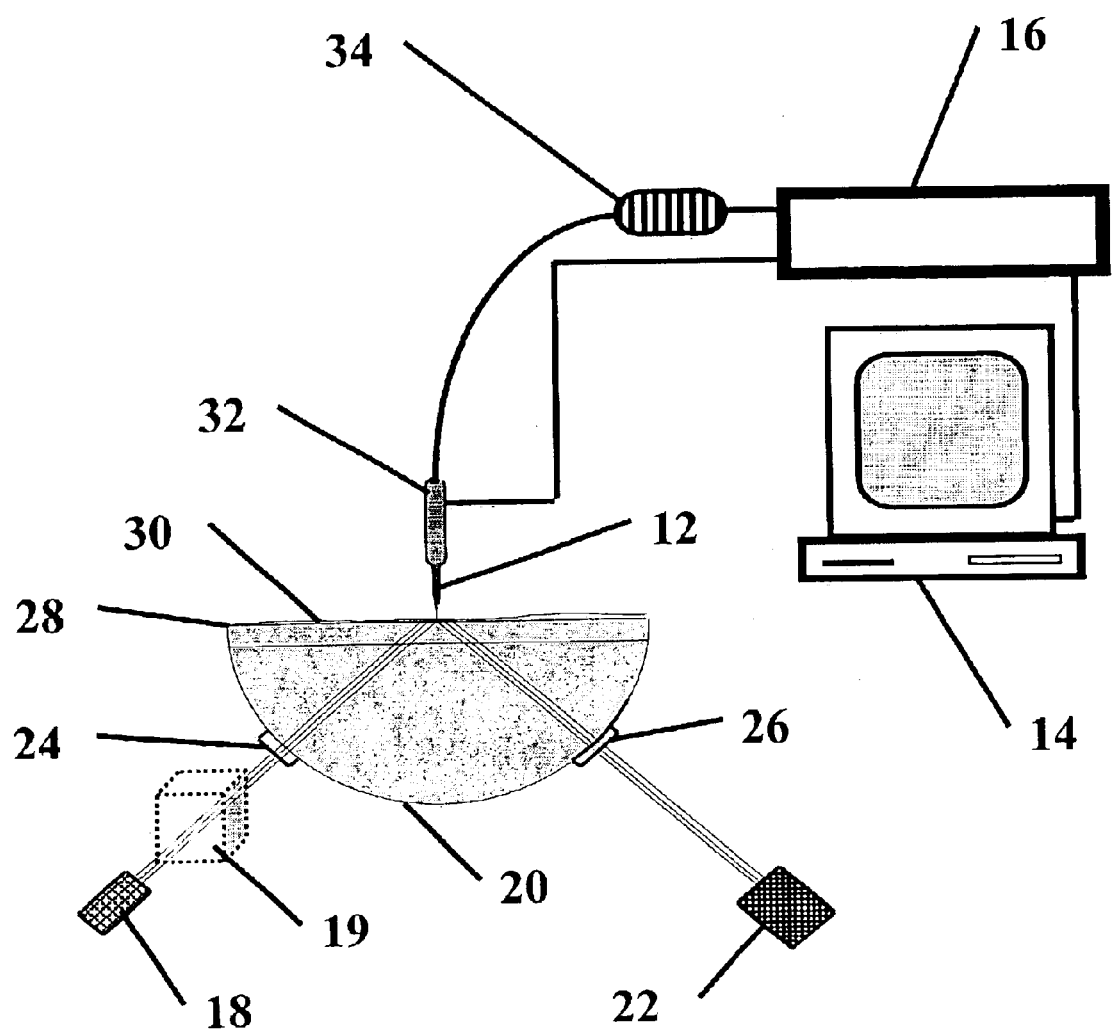
FIG. 1 is a schematic of the major components of the invention.

In the context of this specification, distribution means the temporal or spatial separation of a beam of photons so that the separated parts are each of a given range of wavelengths, this being performed by a device that collects, waveguides, detects, amplifies, or otherwise processes the photons. Surface plasmons are the quanta associated with collective electron motion comprising a longitudinal wave in a material medium. A signal can be spectral information consisting of the intensity of photons within a given range of wavelengths.

Spectrometers are very widely used in science and medicine and industry. Any such spectrometer can be replaced by the instant invention so long as; 1) the sample to be analyzed spectroscopically can be obtained in size to fit the scale of the instant invention without untoward effects on the sample, 2) stray light might otherwise obscure the signal, and 3) provided high-resolution of the wavelengths can be sacrificed for stray-light rejection qualities. Additionally, the application must be one in which the sample can be physically obtained rather than as in remote sensing spectroscopy, except in cases in which sufficient return or transmitted photons can be collected and directed into the subject invention. It may be undesirable in remote sensing to gather a dispersed return signal, but the use of external photon sources, including natural sources, that are located so as to provide photon transmission through a sample and thence into the invention, is desirable for long-range spectroscopic analysis.

This invention finds applications in certain cases wherein it is necessary to spectroscopically analyze, filter, or distribute photon signals. In particular it applies to photons transmitted through or reflected from a sample that is to be spectroscopically analyzed in a manner to minimize the presence of wavelengths that may obscure the signal or saturate the detector, or it is necessary to rapidly spatially separate wavelength content in a controllably varying manner within a small volume. The minimum time quality requires any processing or distribution elements to provide response times of the order of milliseconds.

A variety of compounds may be coated onto the probe in order to provide a surface that is optically selective for targeted compounds reflecting or transmitting photons as a matter of sensing.

A configuration for exciting surface plasmons with photons has been provided by Kretschmann (E. Kretschmann, E., Rather, H., Z. *Naturforsch*, 216, 398–410, (1968)) and by Otto (Otto, A., Z. *Physik*, 216, 398–410, (1968)). In a preferred embodiment of the present invention the Kretschmann configuration is used. The configuration is extended so that a probe or detector is placed within the exponential field of the surface plasmons. In the Kretschmann configuration a beam of photons enters a transparent medium bounded by a flat, thin, metal foil. The polarization component of the beam that lies in the plane of incidence is the only effective component. The beam is directed at an angle of incidence 1 relative to the foil normal such that the energy and momentum of the photons matches that of the surface plasmons (Brewster's angle for media of complex index of refraction). The surface plasmon momentum is proportional to the surface plasmon wave vector K by Planck's constant divided by $2\pi$. Here K is related to the vacuum wave vector k of the incident photons by $K = nk \sin \beta$, where n is the index of refraction of the medium supporting the metal foil. This relation provides conservation of the lateral component of momentum. The frequency and thus the energy of the surface plasmon must equal that of the engendering photon in order to satisfy the conservation of energy. The degree of excitation is then dependent upon the complex index of refraction of the metal foil and is determined by the application of Maxwell's equations and the Cartesian boundary conditions.

A diagram of a preferred embodiment of the present invention is shown in FIG. 1. In this embodiment surface plasmons are engendered by the source beam 18 of photons provided by reflection from or transmission through a sample 19. The source beam 18 is rotated about the center of the surface of the metal foil 30 changing the incident angle of the emitted photons that are reflected from or transmitted through sample 19. Photons enter the cylindrical lens 20 at the optional entrance element 24 and pass through cylindrical lens 20 to impact the bottom surface of metal foil 30 that is coated onto the microscope slide 28. Photons reflected from the foil 30 exit the cylindrical lens 20 through the optional exit element 26 and impact a detector 22. A second source of photons (not shown) that is for reference purposes and emits photons of a known intensity and wavelength may also be incident upon the metal foil 30 within the supporting medium.

A detection device that is spatially arranged at the point of maximum intensity near the metal foil collects each separated energy peak at a given angle of incidence upon the foil. The detection device can be a photosensitive detector or an optical system or waveguide that collects the photons and directs the collected photons to a photosensitive detector. Further, the detection device may be a system that converts the photons to a different energy for purposes of improved propagation in waveguides or for purposes of enhancing the spectral resolution. The detection device in FIG. 1 is positioned in an evanescent near-field generated by the photons being totally reflected at the foil 30. The sample 19 modulates the evanescent near-field and will manifest itself as spatial variations in the near-field intensity at a given height above the foil surface. A fiber optic probe 12 is introduced into the evanescent near-field such that photons will tunnel between the foil 30 and the probe 12. The probe 12 is mounted to one end of a piezoelectric translator 32 so that the probe 12 may be scanned across the foil 30. The translator 32 moves the probe 12 over the foil 30 in a standard raster scan. An end opposite to the probe end of the translator 32 is connected to a photomultiplier tube 34 which detects the photons received by the probe 12. The tube 34 produces an output signal that is proportional to the number of photons received by the probe 12 and provides an electrical current signal proportional to the detected light intensity. This signal drives an electronic feedback circuit 16 which regulates the distance between the probe 12 and the foil 30. The motion of the probe 12 is monitored and controlled by a computer 14, which also serves to collect and process the information generated by the scan of the probe 12 over the foil 30.

Figure 2:
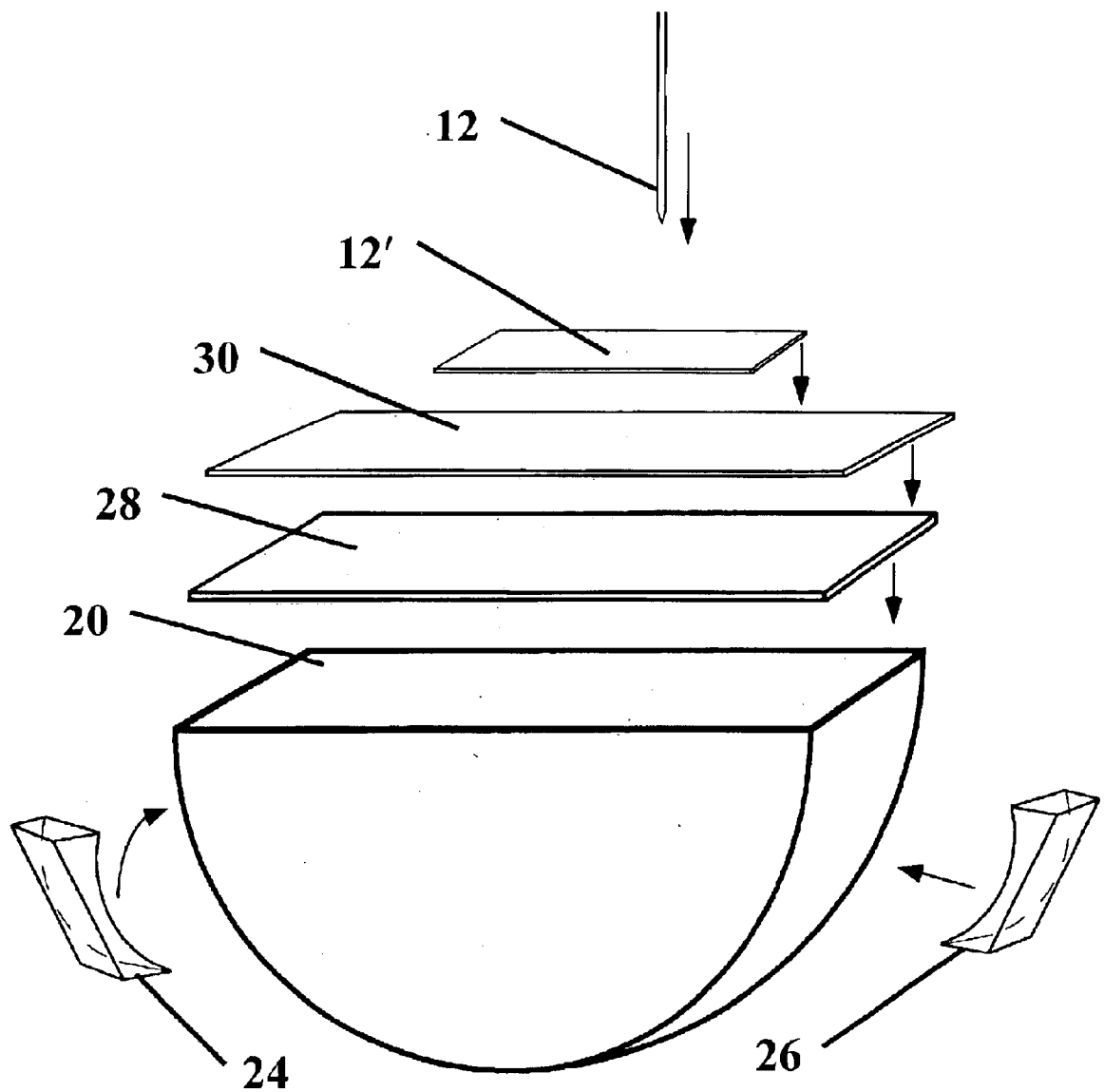
FIG. 2 is an exploded view of the photonic element assembly.

FIG. 2 is an exploded view of a photonic element assembly showing a transparent plano-convex cylindrical lens 20, an optional movable entrance element 24 to prevent focusing of entering photons, an optional movable exit element 26 to prevent defocusing of exiting photons, a slide 28 (such as a microscope slide) mated to the surface of the lens 20 using a photonic gel that matches the index of refraction of the slide 28 and lens 20, a thin metal (typically aluminum, silver, or gold) foil 30 evaporated at nanoscale thickness by vacuum evaporation onto the surface of slide 28, and a detector array 12' or fiber optic probe 12 used to detect photons near the surface of foil 30.

Figure 3:
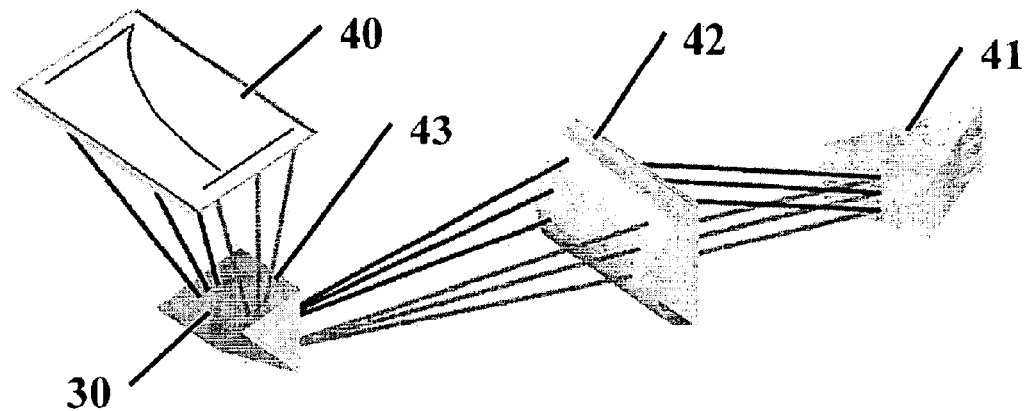
FIG. 3 shows the optics of the embodiment of the invention in which the entire spectrum is displayed on an array detector.

FIG. 3 shows the optics of one embodiment of the invention in which the entire spectrum is displayed on an array detector 40 (schematically represented here as a screen) such as a charge coupled device. The plano-convex cylindrical lens in this case is replaced by a prism 43 having foil 30 on a surface. Photons enter the prism 41 and pass through a two dimensional cylindrical lens 42 to focus the photons incident on the foil 30 surface. The absence of light along the curve on the array detector 40 placed in the exponential field of the surface plasmons (distance exaggerated for clarity) is the surface plasmon dispersion relation and shows up clearly as a curve of varying darkness. A photon of given wavelength will excite the surface plasmon at only a single angle within the tolerance range of milliradians. This results in a dip in the foil reflectivity. The surface plasmon field thus engendered has an exponential decay with distance from the foil and is available on the opposite side of the foil from the incident light. Measurement of the intensity variation along the curve and derivatives thereof provide a measure of the intensity at each wavelength. Spectrometry can be carried out with only slight changes in incident angle.

Figure 4:
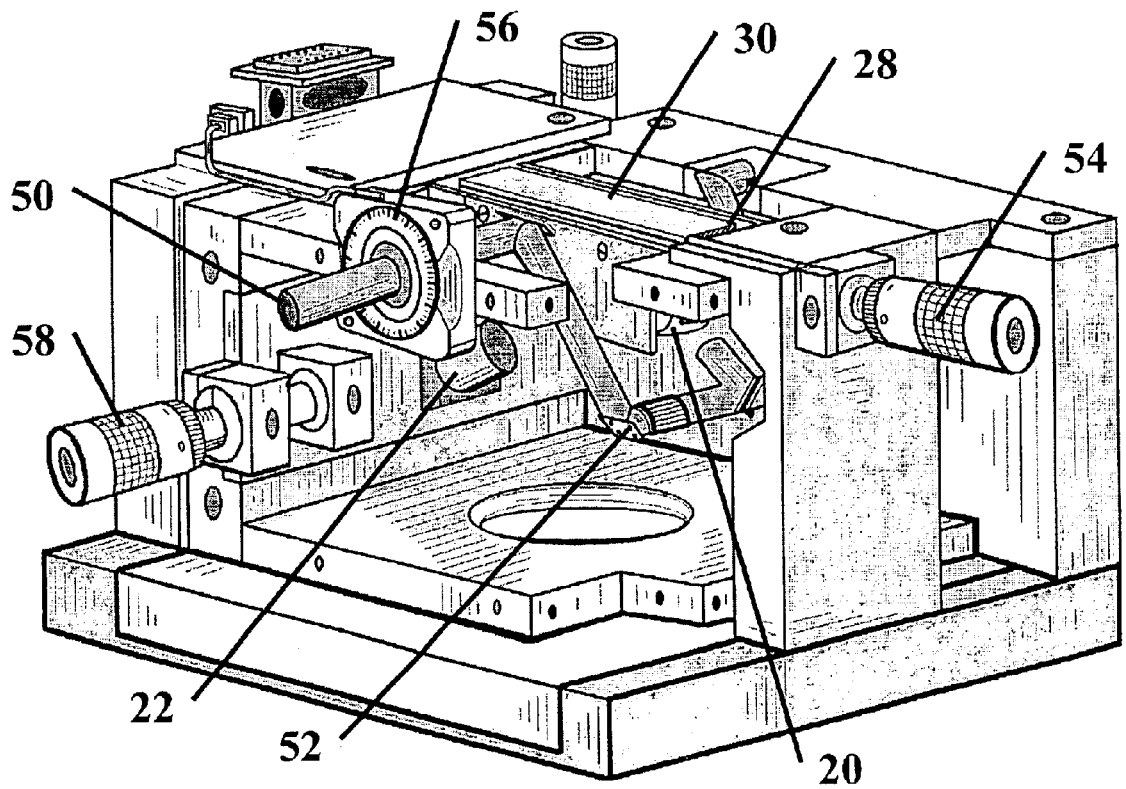
FIG. 4 is the base component of the invention.

FIG. 4 shows the support base of the invention. The incident photons enter from the left into a hollow windlass 50 containing adjustable mirrors 52 at the windlass joints. The photons are directed to fall upon a plano-convex cylindrical lens 20 visible partially in the upper center of the interior. A transparent slide 28 having a nanoscale thickness foil 30 coating is removably disposed on the lens at the top center. A micrometer 54 changes the foil 30 position relative to the lens by moving the transparent slide 28 on the lens 20. The slide 28 is made movable by having an optical gel layer between the slide 28 and the lens 20. In this way the direction of incidence of the photons is altered only by the windlass rotation. The windlass rotation is motorized with an angular positioner 56 with a precision of one tenth of a degree. Other micrometers 58 adjust the overall position of the lens 20 in the orthogonal directions. A detector 22 detects any reflected photons.

Figure 5:
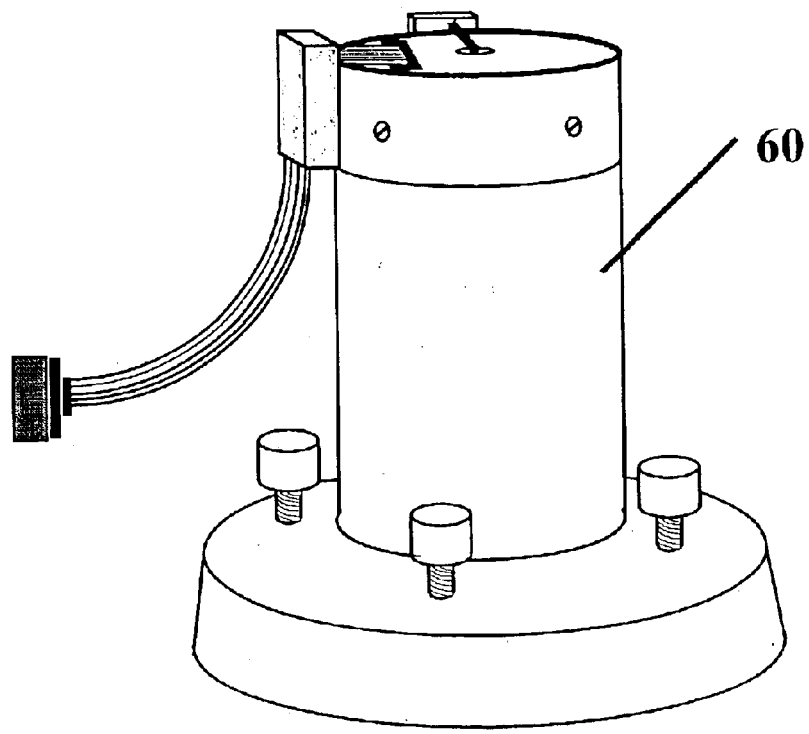
FIG. 5 is a photon probe/detector head.

FIG. 5 shows a preferred embodiment of a photon probe/detector head 60 that is mounted during operation on the top of the base of FIG. 4 and which contains a piezoelectric translator for the probe/detector.

Figure 6:
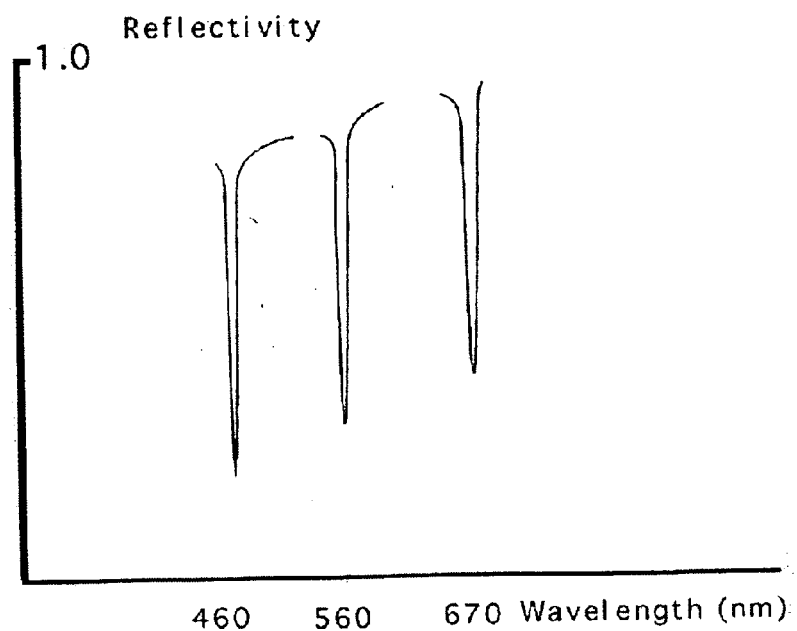
FIG. 6 is a graph showing the surface plasmon excitation reflectance dips, or transmission peaks, versus wavelength.

FIG. 6 is a graph of the surface plasmon excitation reflectance dips (transmission peaks). These show that, if photons at each wavelength are set at the surface plasmon excitation angle in the Kretschmann configuration, then the transmitted photons (those not reflected) at each wavelength have a very small bandwidth permitting spectroscopic resolution on the nanometer scale. Thus, the intensity transmitted at each incident wavelength and corresponding angle of surface plasmon excitation is measured. The collection of measurements in a range of angles comprises the spectrum of the sample without the noise associated with stray light, said stray light being reflected to a very high degree by the metal foil. The spectral resolution may be further improved by using a spectrally sensitive detector with a calibrated wavelength response.

Although a preferred embodiment is described above, it is understood that the invention is capable of numerous rearrangements, modifications and substitutions of parts without departing from the scope of the invention as defined by the appended claims.

What is claimed is:

1. A microoptoelectromechanical integrated spectrometer comprising:
    a photonic element assembly having metal foil removably disposed on a first transparent substrate surface, said substrate having no foil on any other surface;
    a means for directing source photons, that are reflected from or transmitted through a sample, over a range of angles of incidence, into said transparent substrate and onto said metal foil such that source photons are incident at the Brewster angle;
    a means for detecting an induced exponential field in said foil;
    a means for relating said induced exponential field to a known exponential field for said sample to determine the identity of said sample;

wherein said spectrometer performs ultraviolet-to-visible-to-infrared spectroscopy using photon tunneling and surface plasmon excitation.

2. The spectrometer of claim 1 wherein said metal foil is selected from the group consisting of aluminum, silver, and gold.

3. The spectrometer of claim 1 wherein said photonic element assembly further comprises:

an entrance element removably disposed on a second transparent substrate surface, an exit element removably disposed on the second transparent substrate surface, and wherein said metal foil is on a slide removably disposed on said first transparent substrate surface.

4. The spectrometer to claim 3 wherein said metal foil is disposed on said slide in nanoscale thickness.

5. The spectrometer of claim 4 wherein said metal foil is selected from the group consisting of aluminum, silver, and gold.

6. The spectrometer of claim 1 wherein said means for directing source photons is a rotating hollow windlass.

7. The spectrometer of claim 1 wherein said means for detecting the exponential field is an array of charge-coupled devices.

8. The spectrometer of claim 1 wherein said means for detecting the exponential field is a fiber optic probe.

9. The spectrometer of claim 1 wherein said means for relating said induced exponential field to a known exponential field for said sample is a computer.

10. The spectrometer of claim 1 wherein said transparent substrate is a piano-convex cylindrical lens.

11. A spectroscopic method of determining the identity of a sample comprising the steps of:

aligning a sample between source photons and a photonic element assembly having metal removably disposed on a first transparent substrate surface, said substrate having no foil on any other surface;

directing source photons, that are reflected from or transmitted through a sample, over a range of angles of incidence, into said photonic element assembly and onto metal foil such that source photons are incident at the Brewster angle;

detecting an induced exponential field in said foil;

relating said induced exponential field to a known exponential field for said sample to determine the identity of said sample.

12. The spectroscopic method of claim 11 wherein said metal foil is selected from the group consisting of aluminum, silver, and gold.

13. The spectroscopic method of claim 11 wherein said photonic element assembly further comprises:

an entrance element removably disposed on a second transparent substrate surface, an exit element removably disposed on the second transparent substrate surface, and wherein said metal foil is on a slide removably disposed on said first transparent substrate surface.

14. The spectroscopic method of claim 13 wherein said metal foil is disposed on said slide in nanoscale thickness.

15. The spectroscopic method of claim 14 wherein said metal foil is selected from the group consisting of aluminum, silver, and gold.

16. The spectroscopic method of claim 11 wherein said source photons are directed using a rotating hollow windlass.

17. The spectroscopic method of claim 11 wherein said induced exponential field is detected by an array of charge-coupled devices.

18. The spectroscopic method of claim 11 wherein said induced exponential field is detected by a fiber optic probe.

19. The spectroscopic method of claim 11 wherein said induced exponential field is related to a known exponential field for said sample using a computer.

20. The spectroscopic method of claim 11 wherein said photonic element assembly comprises a plano-convex cylindrical lens.

* * * * *